United States Patent [19]
Liu et al.

[11] Patent Number: 5,644,069
[45] Date of Patent: Jul. 1, 1997

[54] SENSOR FOR DISTINGUISHING FUEL VAPORS

[75] Inventors: Yuan Liu; Kenji Motosugi, both of Kawagoe, Japan; Christoph Roth, München, Germany; Tetsu Yamamoto, Kawagoe; Masayuki Arai, Gyoda, both of Japan

[73] Assignee: Hoechst Aktiengesellschaft, Frankfurt, Germany

[21] Appl. No.: 408,437

[22] Filed: Mar. 22, 1995

[30] Foreign Application Priority Data

Mar. 24, 1994 [JP] Japan .................................. 6-054068

[51] Int. Cl.⁶ ........................... G01N 27/12; G01N 31/00
[52] U.S. Cl. ..................... 73/23.2; 73/31.05; 73/23.31; 324/609; 324/663; 324/691; 422/94; 364/509
[58] Field of Search ........................ 73/23.2, 31.05, 73/31.06, 23.31; 324/609, 663, 671, 691, 693; 364/509; 422/94; 338/34

[56] References Cited

U.S. PATENT DOCUMENTS

| | | | |
|---|---|---|---|
| 4,457,161 | 7/1984 | Iwanaga et al. | 73/23 |
| 4,495,793 | 1/1985 | Hager | 73/23 |
| 4,584,867 | 4/1986 | Forster | 73/23 |
| 4,586,143 | 4/1986 | Kaneyasu et al. | 364/509 |
| 4,703,646 | 11/1987 | Müller et al. | 73/23 |
| 4,752,588 | 6/1988 | Ellis et al. | 436/172 |
| 4,887,455 | 12/1989 | Payne et al. | 73/27 R |
| 4,907,441 | 3/1990 | Shurmer | 73/23 |
| 5,217,692 | 6/1993 | Rump et al. | 422/98 |
| 5,272,907 | 12/1993 | Hakala | 73/23.2 |
| 5,448,906 | 9/1995 | Cheung | 73/31.06 |

OTHER PUBLICATIONS

Japanese Abstract 2-85200 published Mar. 26, 1990. Yasuda, H.

Primary Examiner—Hezron E. Williams
Assistant Examiner—J. David Wiggins
Attorney, Agent, or Firm—Curtis, Morris & Safford, P.C.

[57] ABSTRACT

A method for identifying a single fuel vapor in an atmosphere of interest that is selected from the group consisting of at least two fuels and that is the sole fuel component of the atmosphere, comprising the steps of: providing a plurality of measuring means that are at least equal in number to the types of fuels that compose the fuel group and which have different sensitivities to the respective fuel vapors; presetting the relationship between the magnitudes of the outputs from the respective measuring means at various fuel vapor concentrations in such a manner that it differs from one fuel vapor to another; placing said measuring means in the atmosphere of interest containing said single fuel vapor as the sole fuel component; measuring the concentration of that fuel vapor; determining the relationship between the magnitudes of outputs as obtained from the respective measuring means; and comparing the thus determined relationship with the preset relationships, thereby identifying the fuel vapor in the atmosphere of interest. This method enables positive identification of a particular fuel vapor without errors. An apparatus for implementing this method is also provided.

32 Claims, 11 Drawing Sheets

Fig. 3
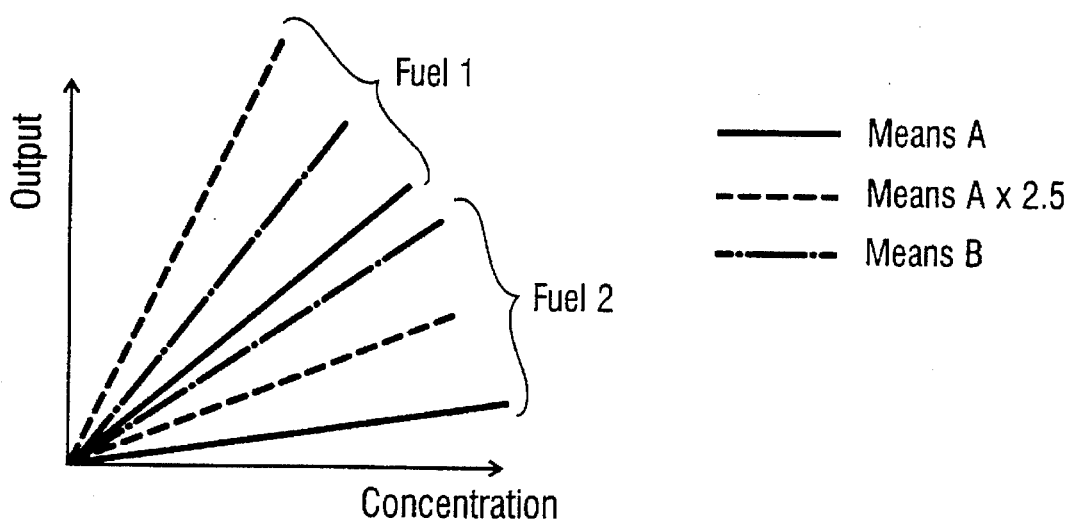
Fig. 4a
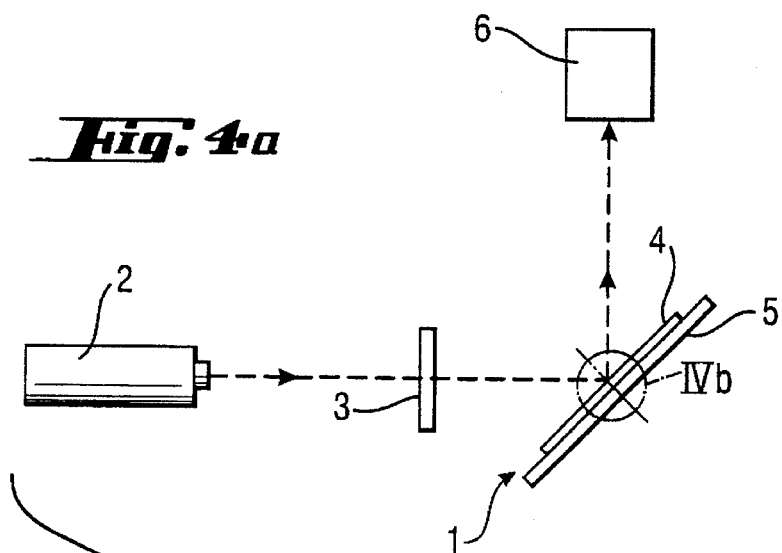
Fig. 4b
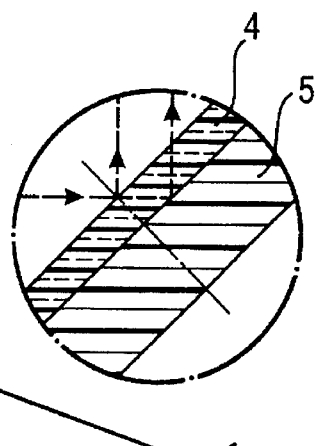
Fig. 4

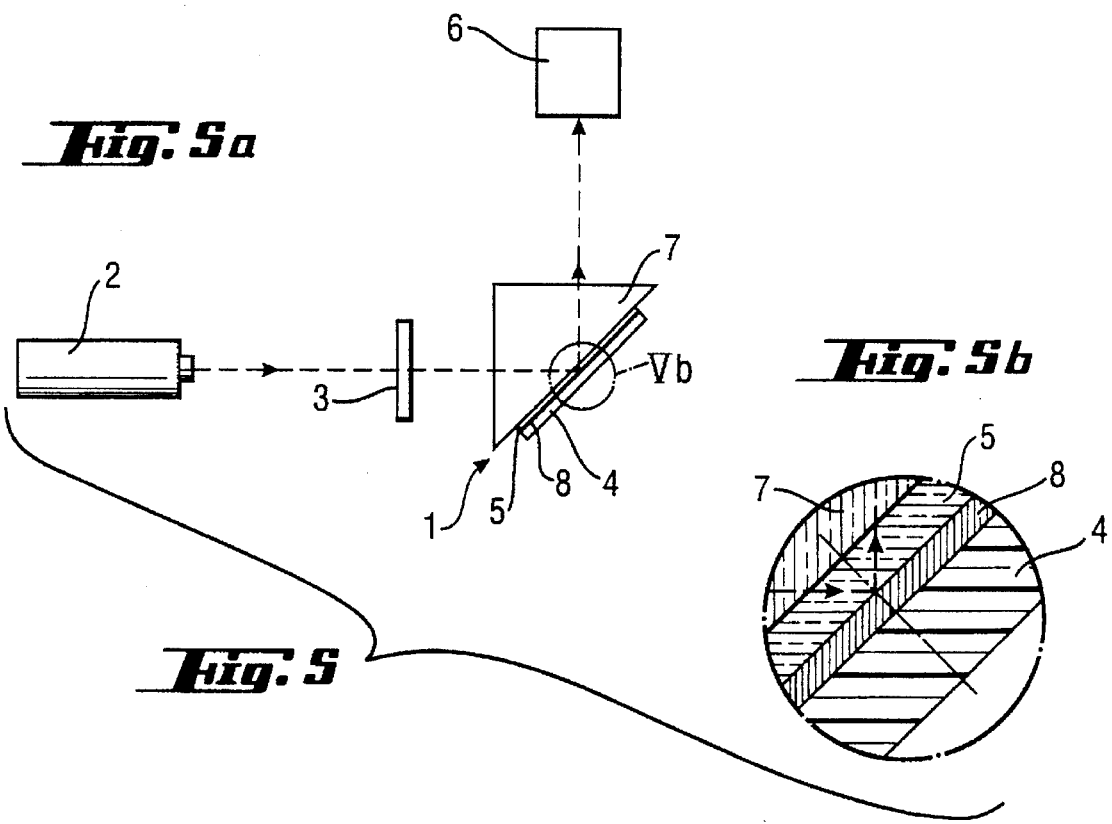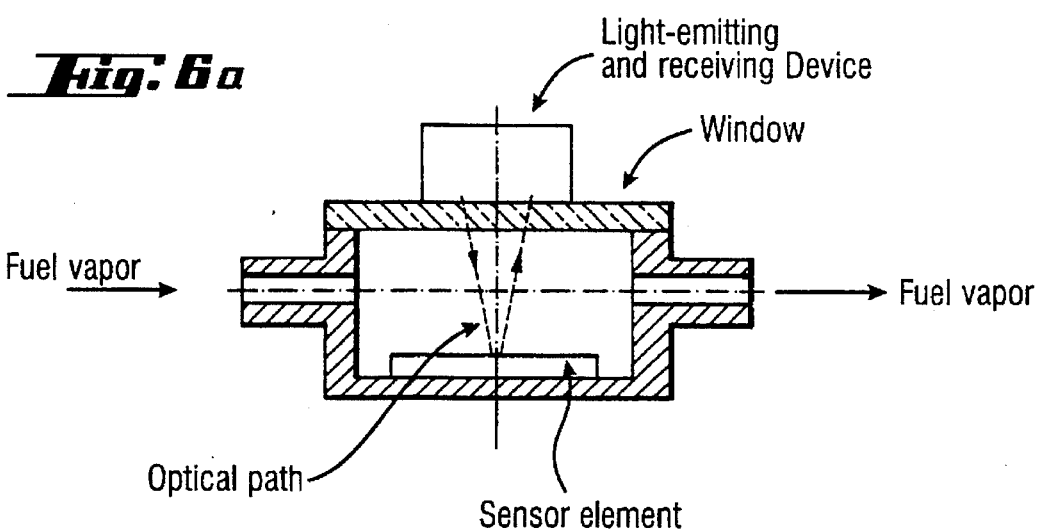

5,644,069

SENSOR FOR DISTINGUISHING FUEL VAPORS

TECHNICAL FIELD

This invention relates to a method for distinguishing a single fuel vapor in an atmosphere of interest that is selected from the group consisting of at least two fuels and that is the sole fuel component of the atmosphere. The invention also relates to an apparatus for implementing this method.

BACKGROUND ART

Several apparatus have been proposed to prevent the filling of automobiles with a wrong fuel by the driver or filling operator at refueling facilities such as filling stations. Examined Japanese Patent Publication (kokoku) Hei 4-64958 discloses an apparatus that uses a gas sensor such as one of a contact burning type; according to the teaching, the fuel vapor in the fuel tank of an automobile to be refueled is aspirated and its concentration is measured to identify the type of the fuel used by the automobile, thereby preventing from filling with a wrong fuel. The device identifies the fuel of interest as gasoline if the measured concentration of the fuel vapor exceeds a preset value or as gas oil (diesel gas oil) if the measured concentration is less than the preset value.

A problem with this apparatus is that since the inlet to the fuel tank remains open to the ambient air atmosphere during refilling, the concentration of the aspirated fuel vapor may potentially be influenced to a great extent by external factors such as weather conditions. If this occurs with a gasoline-fueled car, the gasoline vapor may be diluted with air, causing the apparatus under consideration to read a lower value than it should otherwise and conclude that the automobile to be refueled is a gas oil-fueled car. This possibility cannot be avoided as long as one takes the approach of measuring the absolute values of fuel vapor concentration.

Unexamined Published Japanese Patent Application (kokai) Hei 2-85200 discloses a method for distinguishing a particular oil by the difference in the exhaust sound that develops when the aspirated fuel vapor is discharged through a mechanism having a structure like that of a wind instrument. This method requires that the fuel vapor to be identified be present in a concentration higher than a certain level since the difference in exhaust sound originates from the difference between the densities of two fuel vapors. Hence, the reliability of the method is not assured if the fuel vapor of interest has a very low concentration.

SUMMARY OF THE INVENTION

An object, therefore, of the invention is to provide a method for distinguishing a particular fuel vapor positively without errors.

Another object of the invention is to provide an apparatus for implementing this method.

DISCLOSURE OF THE INVENTION

According to its first aspect, the invention provides a method for distinguishing a single fuel vapor in an atmosphere of interest that is selected from the group consisting of at least two fuels and that is the sole fuel component of the atmosphere. The method starts with providing a plurality of measuring means that are at least equal in number to the types of fuels that compose the fuel group and which have different sensitivities to the respective fuel vapors. Then, the relationship between the magnitudes of the outputs from the respective measuring means at various fuel vapor concentrations is so preset as to differ from one fuel vapor to another. Subsequently, the respective measuring means are placed in the atmosphere of interest containing said single fuel vapor as the sole fuel component and the concentration of that fuel vapor is measured. The relationship between the magnitudes of outputs as obtained from the respective measuring means is determined and compared with the preset relationships, thereby distinguishing the fuel vapor in the atmosphere of interest.

According to the invention, one can identify the type of a particular fuel vapor present in the atmosphere of interest. The prerequisite for the success of the invention is that only one type of fuel vapor be present in the atmosphere of interest and that said fuel vapor be selected from the group consisting of at least two fuels. Consider, for example, the case where the fuel to be identified is selected from the group consisting of gasoline, gas oil and methanol. The method of the invention is applicable with success to distinguishing the type of one of these fuels on the condition that an atmosphere of interest contains only one type of fuel vapor selected from among these fuels and that the type of said fuel is unknown.

BRIEF DESCRIPTION OF THE DRAWINGS

FIG. 3 shows yet another example of the relationship between the concentration of fuel vapor and the output of measuring means for two different types of fuel and measuring means;

FIG. 4 shows the layout of an optical sensor relying upon IER for its operation;

FIG. 5 shows the layout of an optical sensor relying upon SPR for its operation;

FIG. 6 shows the layout of an optical sensor relying upon IER for its operation;

BEST MODE FOR CARRYING OUT THE INVENTION

The measuring means to be used in the invention are at least equal in number to the types of fuels that compose the fuel group. Any measuring means may be used as long as they produce output (e.g. monotonically increasing or decreasing output or output of a periodic function) in the presence of the fuel vapors of interest with certain reproducibility and if they have different sensitivities to the respective fuel vapors. As will be described hereinafter, it is preferred to use an optical sensor as the measuring means in the invention.

Consider here the case of differentiating between two fuels 1 and 2. To this end, two measuring means A and B are used. Let us also assume that the measuring means A and B are so selected that throughout the range of fuel vapor concentrations to be measured, the output of measuring means A in response to the vapor of fuel 1 is greater than that of means B whereas the output of measuring means B in response to the vapor of fuel 2 is greater than that of means A; then, the relationship between the magnitudes of the outputs of the two measuring means is so set as to differ from one fuel vapor to the other. In other words, the relationship $Va>Vb$ is preset for fuel 1 and the relationship $Va<Vb$ is preset for fuel 2, Va being the output of the measuring means A and Vb being the output of the measuring means B. In the next step, both measuring means A and B are placed in an atmosphere of interest that contains either fuel 1 or 2 and the concentration of the fuel in it is measured by the two means. If $Va>Vb$, one may safely conclude from FIG. 1 that the fuel vapor in the atmosphere of interest is that of fuel 1; if $Va<Vb$, the fuel in the atmosphere is that of fuel 2.

Figure 1:
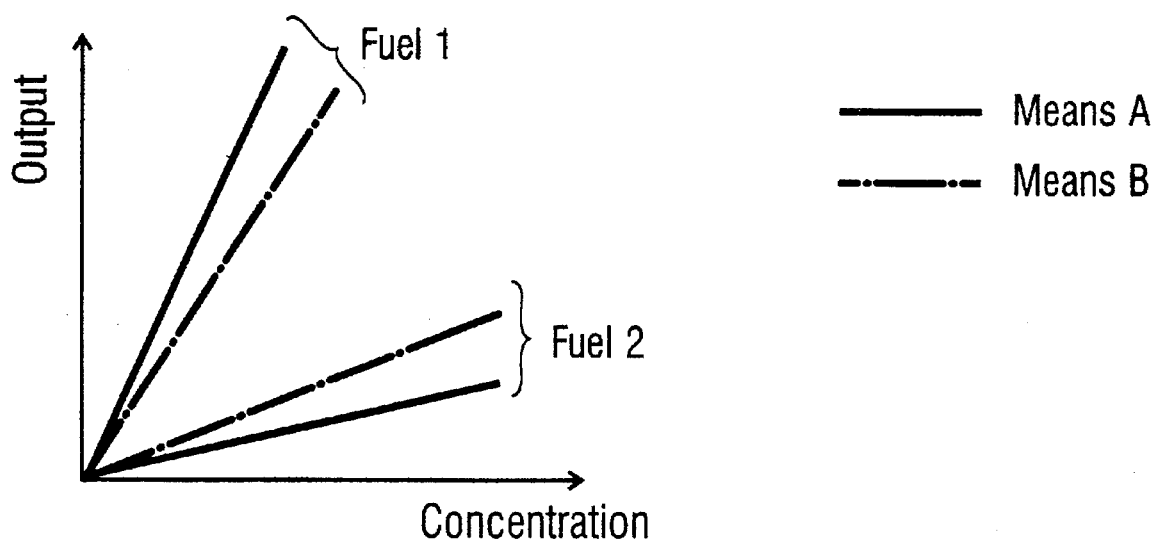
FIG. 1 shows an example of the relationship between the concentration of fuel vapor and the output of measuring means for two different types of fuel and measuring means.

To differentiate between fuel vapors, the invention uses an apparatus that includes not only the measuring means described above but also output comparator means for comparing the magnitudes of the outputs from the respective measuring means. The output comparator means is so adapted that the relationship between the magnitudes of the outputs from the respective measuring means at various fuel vapor concentration differs from one fuel vapor to another as illustrated in FIG. 1. The outputs from the respective measuring means are fed into this output comparator means, which determines the relationship between the magnitudes of the respective outputs. The comparator means then compares the thus determined relationship With the preset relationships (as shown in FIG. 1) to identify the type of the fuel vapor present in the atmosphere of interest.

Either an analog or digital electronic circuit may be used as the output comparator means. The output of each measuring means is subtracted from the output as produced in the absence of fuel vapors and then the net relationship between the magnitudes of the outputs from the respective measuring means is determined. To determine this relationship and compare it with the preset relationships, a comparator may be used as output comparator means in the form of an analog electronic circuit. If a digital circuit is used as the output comparator means, analog-to-digital conversion may be followed by processing with a logic circuit or a microcomputer.

Figure 2:
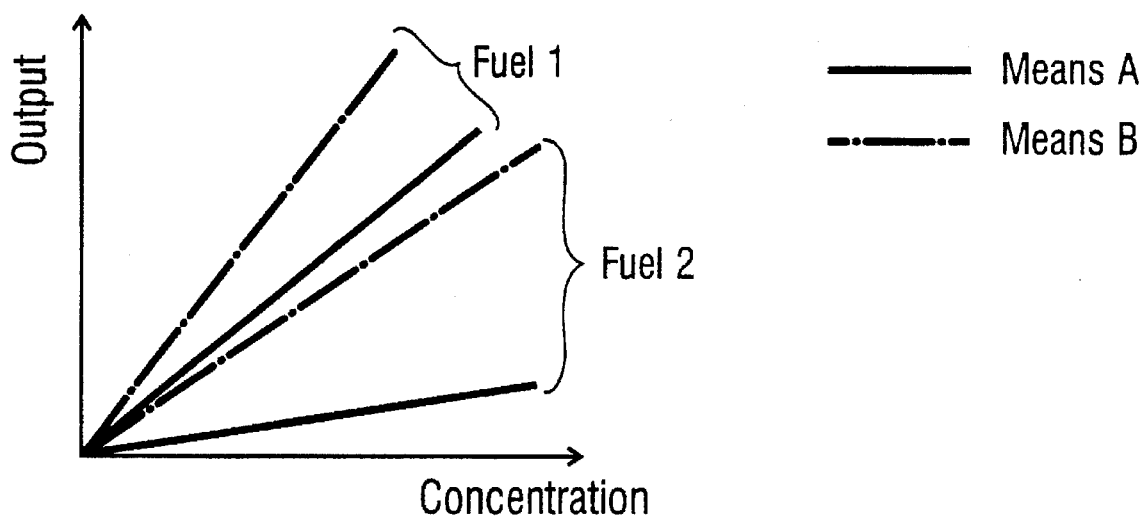
FIG. 2 shows another example of the relationship between the concentration of fuel vapor and the output of measuring means for two different types of fuel and measuring means.

If certain cases, the relationships between the magnitudes of outputs as actually obtained from the measuring means A and B may not be as shown in FIG. 1 but as in FIG. 2. If this is the case, determination of the relationship between the magnitudes of the outputs from respective measuring means is preceded by performance of an "arithmetic calculation" on at least one of those outputs. A preferred example of such arithmetic calculations is multiplication by a proportionality constant. If the outputs of measuring means A shown in FIG. 2 are multiplied by 2.5, the result will be as shown in FIG. 3 and it satisfies the same relationships as shown in FIG. 1. Thus, the concept of the invention is applicable to the case shown in FIG. 2 if a suitable "arithmetic calculation" is performed.

For successful practice of the invention, the number of measuring means to be used must at least be equal to the number of fuel candidates to be differentiated. If necessary, more measuring means may be used and this offers the advantage of preventing misidentification of the fuel type of interest even if either one of the measuring means fails to functions properly. Consider, for example, the case of placing measuring means A and B in an atmosphere of interest that contains either fuel 1 or 2. Let us also assume that the relationship between the magnitudes of outputs from the respective measuring means is preset to be $Va>Vb$ for fuel 1 and $Va<Vb$ for fuel 2. If either one of the measuring means malfunctions to produce the output relationship $Va>Vb$ in spite of the fact that the atmosphere contains fuel 2, the output comparator means will misidentify the fuel vapor of interest as that of fuel 1. To avoid this possibility, one may add a third measuring means C and preset the relationship between the magnitudes of outputs from the respective measuring means in such a way that it is $Vc>Va>Vb$ for fuel 1 and $Vb>Va>Vc$ for fuel 2, with Vc representing the output of the additional measuring means C. If this is the case, malfunctioning of the means A or B will result in the production of the output relationship $Va>Vb>Vc$; since this relationship is not included in the preset data, the output comparator means will not perform any assigned job, thereby preventing misidentification of fuel type. If desired, the output comparator means may be adapted to issue an error signal that notifies the operator of the malfunctioning of measuring means.

In accordance with the invention, the relationship between the magnitudes of outputs as produced from the respective measuring means, or comparison between the relative values of the respective outputs, is relied upon to perform fuel type identification. Therefore, the dynamic range of identification is expanded and the correct result is assured not only at high fuel vapor concentrations but also at very low concentrations.

The measuring means may be of any type of gas sensors such as those that depend on a semiconductor, contact burning, photochemical reaction, infrared radiation and thermistor gas sensor and which are capable of interacting with the vapor from a fuel to detect its presence. Since fuels to be handled by the invention are flammable, it is desirable to use optical sensors having high explosion-proof quality. A preferred optical sensor that satisfies this requirement comprises a sensor element that has a thin polymeric film on a substrate, as well as optical measuring means capable of optical measurement of physical changes that occur in the polymeric film. A plurality of measuring means can be established by properly selecting thin polymeric films of different types.

A preferred thin polymeric film comprises a homo- or copolymer having a recurring unit of the following formula (I):

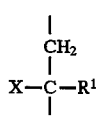

(I)

wherein X is —H, —F, —Cl, —Br, —CH₃, —CF₃, —CN or —CH₂—CH₃; R¹ is —R² or —Z—R², wherein Z is —O—, —S—, —NH—, —NR²'—, —(C=Y)—, —(C=Y)—Y—, —Y—(C=Y)—, —(SO₂)—, —Y'—(SO₂)—, —(SO₂)—Y'—, —Y'—(SO₂)—Y'—, —NH—(C=O)—, —(C=O)—NH—, —(C=O)—NR²'—, —Y'—(C=Y)—Y'— or O—O—(C=O)—(CH₂)ₙ—(C=O)—O— wherein Y is O or S, Y' is O or NH, n is an integer of 0 to 20, R² and R²' are each independently a hydrogen atom, linear alkyl group, branched alkyl group, cycloalkyl group, unsaturated hydrocarbon group, aryl group, saturated or unsaturated hetero ring group or substituted forms thereof; provided that R¹ is not a hydrogen atom, a linear alkyl group or a branched alkyl group.

In formula (I), X is preferably H or CH₃, R¹ is preferably a substituted or unsubstituted aryl group or —Z—R², in which Z is preferably —O—, —(C=O)—O— or —O—(C=O)—, and R² is preferably a linear alkyl group, branched alkyl group, cycloalkyl group, saturated hydrocarbon group, aryl group, saturated or unsaturated hereto ring or substituted forms thereof.

The polymer to be used in the thin polymeric film may be a homopolymer solely composed of the single recurring unit (I) or it may be a copolymer containing another recurring unit or a copolymer that consists of two or more species of the recurring unit (I). The recurring units may be arranged in any order or fashion in the copolymers, which hence may be a random copolymer, an alternating copolymer, a block copolymer or a graft copolymer.

In a particularly preferred case, the thin polymer film may be prepared from polymethacrylic acid esters or polyacrylic acid esters. The esters have preferably linear or branched alkyls or cycloalkyls as pendant groups which have preferably 4–22 carbon atoms.

Polymers that are particularly preferred for use in the thin polymeric film are listed below:
poly(dodecyl methacrylate);
poly(isodecyl methacrylate);
poly(2-ethylhexyl methacrylate);
poly(2-ethylhexyl methacrylate-co-methyl methacrylate);
poly(2-ethylhexyl methacrylate-co-styrene);
poly(methyl methacrylate-co-2-ethylhexyl acrylate);
poly(methyl methacrylate-co-2-ethylhexyl methacrylate);
poly(isobutyl methacrylate-co-glycidyl methacrylate);
poly(cyclohexyl methacrylate);
poly(octadecyl methacrylate);
poly(octadecyl methacrylate-co-styrene);
poly(vinyl propionate);
poly(dodecyl methacrylate-co-styrene);
poly(dodecyl methacrylate-co-glycidyl methacrylate);
poly(butyl methacrylate);
poly(butyl methacrylate-co-methyl methacrylate);
poly(butyl methacrylate-co-glycidyl methacrylate);
poly(2-ethylhexyl methacrylate-co-glycidyl methacrylate);
poly(cyclohexyl methacrylate-co-glycidyl methacrylate);
poly(cyclohexyl methacrylate-co-methyl methacrylate);
poly(benzyl methacrylate-co-2-ethylhexyl methacrylate);
poly(2-ethylhexyl methacrylate-co-diacetoneacrylamide);
poly(2-ethylhexyl methacrylate-co-benzyl methacrylate-co-glycidyl methacrylate);
poly(2-ethylhexyl methacrylate-co-methyl methacrylate-co-glycidyl methacrylate);
poly(vinyl cinnamate);
poly(vinyl cinnamate-co-dodecyl methacrylate);
poly(tetrahydrofurfuryl methacrylate);
poly(hexadecyl methacrylate);
poly(2-ethylbutyl methacrylate);
poly(2-hydroxyethyl methacrylate);
poly(cyclohexyl methacrylate-co-isobutyl methacrylate);
poly(cyclohexyl methacrylate-co-2-ethylhexyl methacrylate);
poly(butyl methacrylate-co-2-ethylhexyl methacrylate);
poly(butyl methacrylate-co-isobutyl methacrylate);
poly(cyclohexyl methacrylate-co-butyl methacrylate);
poly(cyclohexyl methacrylate-co-dodecyl methacrylate);
poly(butyl methacrylate-co-ethyl methacrylate);
poly(butyl methacrylate-co-octadecyl methacrylate);
poly(butyl methacrylate-co-styrene);
poly(4-methylstyrene);
poly(cyclohexyl methacrylate-co-benzyl methacrylate);
poly(dodecyl methacrylate-co-benzyl methacrylate);
poly(octadecyl methacrylate-co-benzyl methacrylate);
poly(benzyl methacrylate-co-tetrahydrofurfuryl methacrylate);
poly(benzyl methacrylate-co-hexadecyl methacrylate);
poly(dodecyl methacrylate-co-methyl methacrylate);
poly(dodecyl methacrylate-co-ethyl methacrylate);
poly(2-ethylhexyl methacrylate-co-dodecyl methacrylate);
poly(2-ethylhexyl methacrylate-co-octadecyl methacrylate);
poly(2-ethylhexyl methacrylate-co-benzyl methacrylate);
poly(tetrahydrofurfuryl methacrylate-co-glycidyl methacrylate);
poly(styrene-co-octadecyl acrylate);
poly(octadecyl methacrylate-co-glycidyl methacrylate);
poly(4-methoxystyrene);
poly(2-ethylbutyl methacrylate-co-glycidyl methacrylate);
poly(styrene-co-tetrahydrofurfuryl methacrylate);
poly(2-ethylhexyl methacrylate-co-propyl methacrylate);
poly(octadecyl methacrylate-co-isopropyl methacrylate);
poly(3-methyl-4-hydroxystyrene-co-4-hydroxystyrene); and
poly(styrene-co-2-ethylhexyl methacrylate-co-glycidyl methacrylate).

The above-listed homo- or copolymers of methacrylate esters may be replaced by homo- or copolymers of acrylate esters.

The polymers described above may be crosslinked either by themselves or by introducing compounds that have crosslinking reactive groups. Examples of crosslinking reactive groups include an amino group, a hydroxyl group, a carboxyl group, an epoxy group, a carbonyl group, a urethane group and derivatives thereof. Another example is a C=C double bond. Exemplary compounds having this double bond include maleic acid, fumaric acid, sorbic acid, itaconic acid, cinnamic acid and derivatives thereof. Also useful as crosslinking agents are substances that have chemical structures capable of forming carbenes or nitrenes upon exposure to visible light, ultraviolet light or high-energy radiations. One great advantage of crosslinking the polymers is that the films formed of crosslinked polymers are insoluble and hence have increased stability. There is no particular limitation on the crosslinking method that can be employed and any known techniques such as heating and exposure to light and other radiations may be adapted.

Any known thin-film forming technologies can be used to form thin polymeric films from the polymers described above. Examples include spin coating, the casting of polymer solutions and melt extrusion. The thickness of the polymer is preferably as small as possible and, hence, it is particularly preferred to adopt suitable techniques such as spin coating which are capable of forming very thin polymer films.

If a shorter response time is required by the optical measuring means that employ thin polymeric films, it is desirable to use film-forming polymers that have lower glass transition points than the temperature of the environment for measurement.

The physical or chemical changes in the thin polymeric film that may be used in the invention are preferably those which occur as a result of the polymer film having reacted with a fuel vapor of interest or those which are caused by its absorption by or adsorption on the film. Such interactions with the fuel vapor of interest will cause swelling of the thin polymeric film, thereby changing its thickness or refractive index. The physical changes in the thin polymeric film will respond so quickly to the changes in the concentrations of fuel vapors that there is no particular need to take the time lag of measurement into account. For practical purposes, measuring the physical changes that occur 0.5–1.0 second after the change in the concentration of a fuel vapor of interest will suffice. It is preferred for the purposes of the invention to measure the change in the product of the thickness and refractive index of the thin polymer film. While various methods are known to be capable of measuring the change in the product of the thickness and refractive index of the thin polymer film, it is particularly preferred to use interference enhanced reflection (IER), surface plasmon resonance (SPR) and optically guided Mach-Zehnder interferometry.

IER is a method that utilizes the reflection characteristic of the thin polymer film on a highly reflective substrate. The light reflected from the surface of the thin polymer film and the light reflected from the interface between the thin polymer film and the substrate will interfere with each other. The intensity of reflected light is largely dependent on the thickness and refractive index of the polymer film. In other words, the change in the thickness or refractive index of the thin polymer film or the changes in both two parameters can be observed as the change in the intensity of reflected light. Thus, the physical change in the thin polymeric film that is utilized by IER is the change in the thickness and refractive index of the film.

A system layout of an optical sensor that relies upon IER for its operation is shown in FIG. 4. Light to be launched into a sensor element 1 having the thin polymeric film on a substrate is issued from a light source 2. An example of the light source 2 is a laser or a light-emitting diode (LED). An exemplary laser is a He-Ne laser. The light issued from the light source 2 is first launched into a polarizer 3 which polarizes the incident light in a direction perpendicular to the entrance face of the sensor element 1. The polarized incident light then enters the sensor element 1 and is reflected partly by the surface of the thin polymer film 4 and partly by the interface between the film 4 and the substrate 5. The two beamlets of the reflected light interfere with each other and are thereafter supplied to a photodetector 6 for conversion to an electric signal. The photodetector 6 generates an electric signal proportional to the intensity of the light it receives. An example of the photodetector 6 is a photodiode or a phototransistor. The generated electric signal is sent to output comparator means. A plurality of such optical sensors are used and the relationship between the magnitudes of the respective sensors is determined and compared with the preset relationships by the comparator means so as to identify the fuel type of interest.

SPR is a method of detecting properties of the polymeric thin film by excitation of surface plasmon resonances in a metal surface. In SPR, when light is incident upon a thin metal film at the critical angle in such a way that the momentum and energy of the photons coincide with those of a surface plasmon in the metal, the energy of the photons will be coupled into the surface plasmon, causing a sharp drop in the intensity of reflected light. The occurrence of such coupling with surface plasmons is highly sensitive to the thickness of the metal film and the dielectric characteristics of the thin polymer film on the other side of the metal film. Thus, the physical change in the thin polymer film that is utilized by SPR is also the change in the thickness and refractive index of the film.

A system layout of an optical sensor that relies on SPR for its operation is shown in FIG. 5. Sensor element 1 comprises a transparent substrate 5 such as a slide glass that is overlaid with a thin metal (e.g. silver or gold) film 8 which in turn is overlaid with a thin polymeric film 4. Light emitted from a light source 2 is TM-polarized by means of a polarizer 3, launched into a right-angle prism 7 placed on the transparent substrate 5, then incident upon and reflexed from the thin metal film 8. An example of the light source 2 is a laser or a light-emitting diode (LED). An exemplary laser is a He-Ne laser. For index matching of the prism 7 and the transparent substrate 5, the gap between the two members may be filled with an immersion oil. The assembly of the prism and the substrate-metal-polymer combination is placed within a flow-through cell (not shown) in such a way that the thin polymer film 4 faces the inside of the cell. With the fuel vapor containing atmosphere of interest being allowed to flow through the cell, the intensity of reflected light is measured with a photodetector 6. The photodetector 6 generates an electric signal proportional to the intensity of the light it receives. An example of the photodetector 6 is a photodiode or a phototransistor. The generated electric signal is sent to output comparator means. A plurality of such optical sensors are used and the relationship between the magnitudes of the respective sensors is determined and compared with the present relationships by the comparator means so as to identify the fuel type of interest.

In another embodiment of the measurement by IER or SPR, the sensor element 1 shown in FIG. 4 or 5 may be modified to include an array of thin polymer films formed on a common substrate that admit the entrance of light from the light source 2. If more than one light source 2 is to be used, the number of light sources may be equal to that of polymer films. Alternatively, light from a single light source may be split into more than one beam by means of fiber optics so that they are launched into the sensor element 1. The beams reflected from the sensor element 1 are converted to electric signals by means of as many photodetectors 6 as the thin polymer films.

In still another embodiment of the measurement by IER or SPR, the light source 2 and the photodetector 6 which are shown in FIGS. 4 and 5 may be combined to form an integral assembly, as exemplified by a device that is generally composed of a light-emitting diode and a phototransistor in integral combination. Commercial versions of this device are available under such trade names as "PHOTOREFLECTOR" or "PHOTOSENSOR". Using these devices offers the advantage of downsizing the overall system of fuel identification.

The thin polymeric film is used together with the substrate for supporting the film. The type of such substrate varies with the type of means for detecting the physical changes to be experienced by the thin polymer film. If IER is to be adopted, the substrate may be formed of a silicon wafer, glass, a polymer, a metal or the like. If SPR is to be adopted, glass or a clear polymer overlaid with a thin metal (e.g. Ag or Au) film may be employed.

The result of fuel type identification by the output comparator means may be sent to output means and thence supplied either as an electric signal (e.g. a voltage signal, a current signal or a contact signal) or as an optical signal (e.g. an intensity signal or a frequency signal).

The apparatus of the invention can be fabricated as a small and lightweight product at low cost. These features, combined with the essential safety of the optical sensor it uses, the apparatus can be attached to a refilling nozzle and this makes it possible to achieve even faster identification of a particular fuel type.

It should also be noted that the invention is applicable not only to the identification of fuel vapors but also to areas where it is necessary to identify the types of other gases.

The following examples are provided for the purpose of further illustrating the invention but are in no way to be taken as limiting.

EXAMPLE 1

The method of the invention was applied to distinguish between gasoline and gas oil by using IER.

Figure 7:
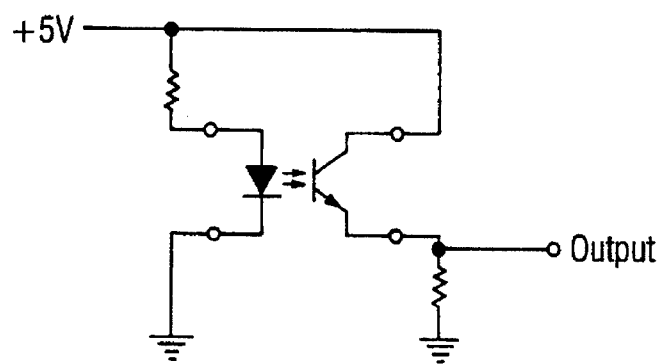
FIG. 7 shows the circuit of a light emitting and receiving device.

The measuring means used in this example had the construction shown in FIG. 6. It was composed of a sensor element (i.e. a thin polymeric film spin coated in a thickness of about 400 nm on a silicon substrate) and a light-emitting and receiving element comprising an integrated assembly of an LED and a phototransistor each having a center wavelength of 940 nm. The light-emitting and receiving element was driven with an electric circuit (see FIG. 7) and the collector current through the phototransistor was measured as the voltage across the resistor between the emitter and the ground. The thus measured voltage was the output of the measuring means.

Figure 8:
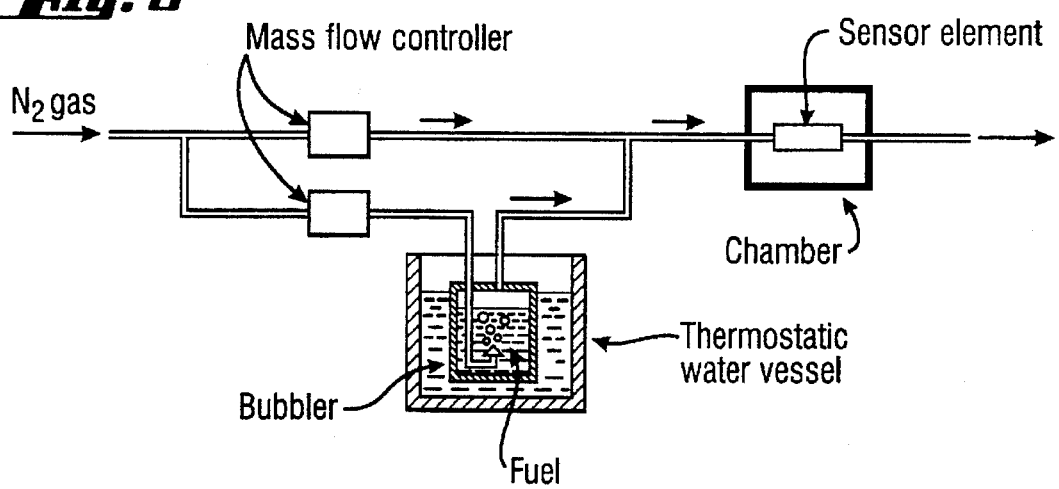
FIG. 8 shows a vapor generator.
Figure 9:
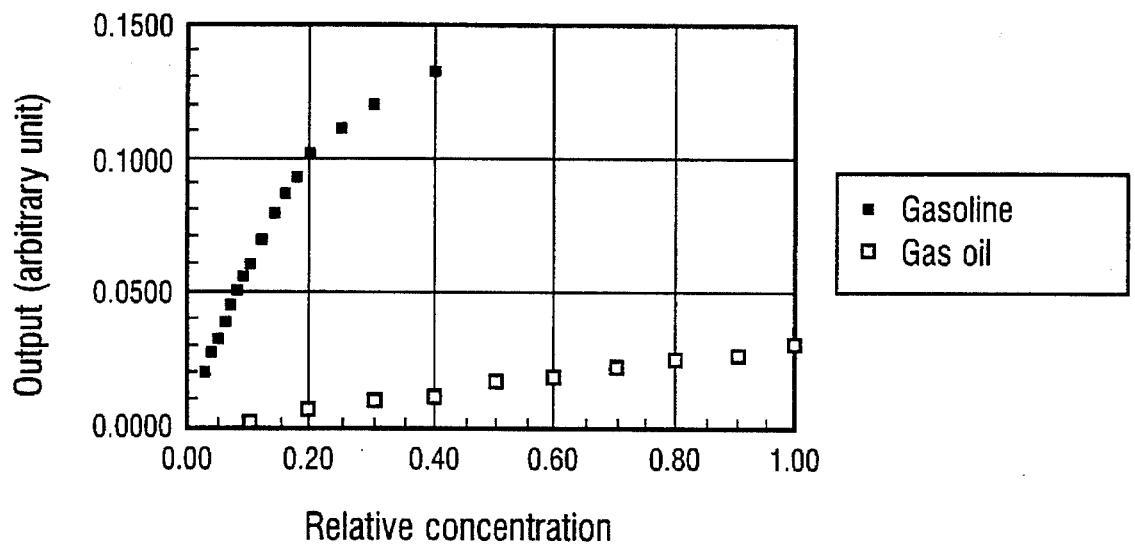
FIG. 9 shows the sensitivity characteristics of the measuring means A used in Example 1.
Figure 10:
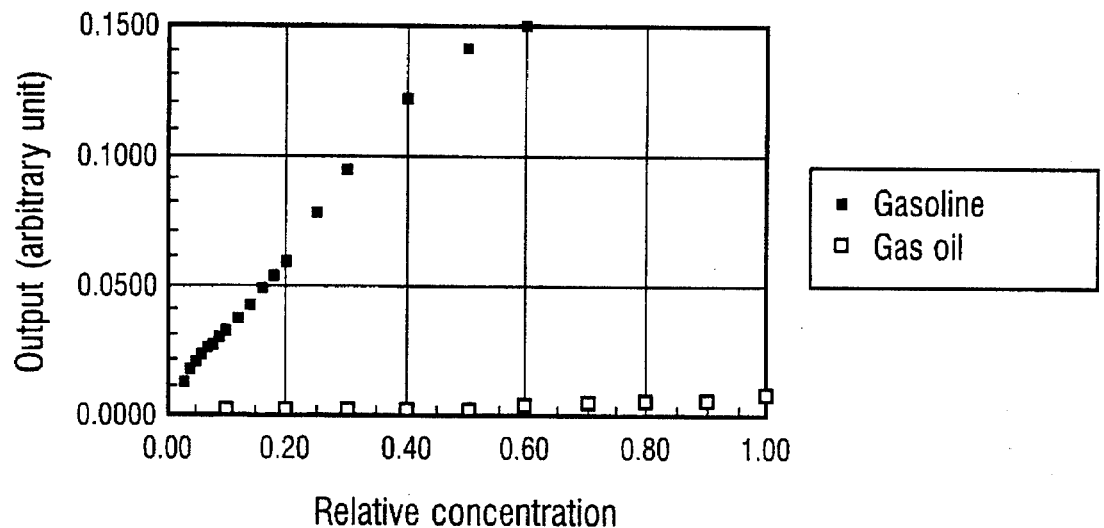
FIG. 10 shows the sensitivity characteristics of the measuring means B used in Example 1.
Figure 11:
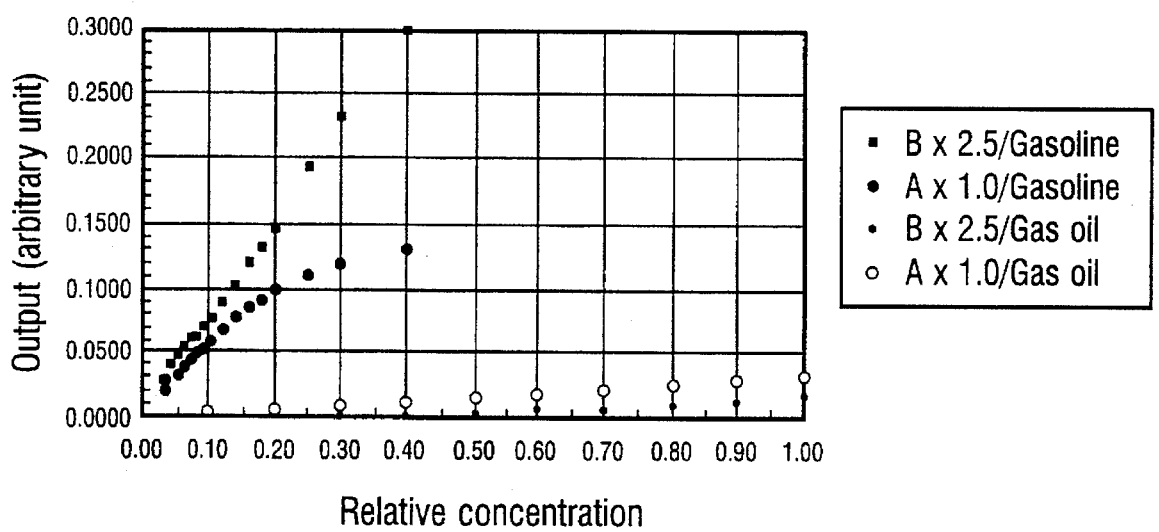
FIG. 11 shows the sensitivity characteristics of the measuring means A and B used in combination in Example 1 with their outputs being multiplied by proportionality constants 1 and 2.5, respectively.

Fuel vapors of varying concentrations were evolved by means of a vapor generator (see FIG. 8) and supplied to the measuring means described above. Two types of measuring means were used; one was composed of a thin poly(styrene-co-octadecyl acrylate) film (measuring means A) and the other composed of a thin poly(styrene-co-2-ethylhexyl methacrylate-co-glycidyl methacrylate) film (measuring means B). The sensitivity characteristics of the two measuring means to gasoline and gas oil vapors were measured and the results are shown in FIGS. 9 and 10, respectively. The term "sensitivity" means the difference between the output of measuring means as produced one second after the supply of a fuel vapor of a given concentration and the output of the same measuring means as supplied with nitrogen gas. The "relative concentration" plotted along the horizontal axis of each figure represents the ratio of the concentration of a fuel vapor in the environment of measurement to its saturation concentration. The operation of the fuel vapor distinguishing system containing the two measuring means will now be described with reference to FIG. 11, in which the output values of measuring means A are plotted as such (multiplied by unity) whereas the output values of measuring means B are plotted as multiplied by 2.5. In the case of gas oil vapor, the relationship between the magnitudes of outputs from measuring means A and B is expressed by Va<Vb irrespective of the vapor concentration; in the case of gas oil vapor, the output relationship is expressed by Va>Vb. Therefore, if the outputs from the two measuring means satisfy the relationship Va<Vb, the vapor of interest may well be identified as gasoline vapor irrespective of its concentration; if Va>Vb, gas oil vapor may be the identify of the vapor being measured.

EXAMPLE 2

The method of the invention was applied to distinguish between gasoline, diesel oil and methanol by using IER as in Example 1.

Three sensor elements were provided; they were measuring means A including a thin poly(2-ethylhexyl methacrylate-co-glycidyl methacrylate) film, measuring means B including a thin poly(octadecyl methacrylate-co-glycidyl methacrylate) film, and measuring means C including a thin poly(3-methyl-4-hydroxystyrene-co-4-hydroxystyrene) film. Each film was formed by spin coating in a thickness of about 400 nm on a silicon substrate.

Figure 12:
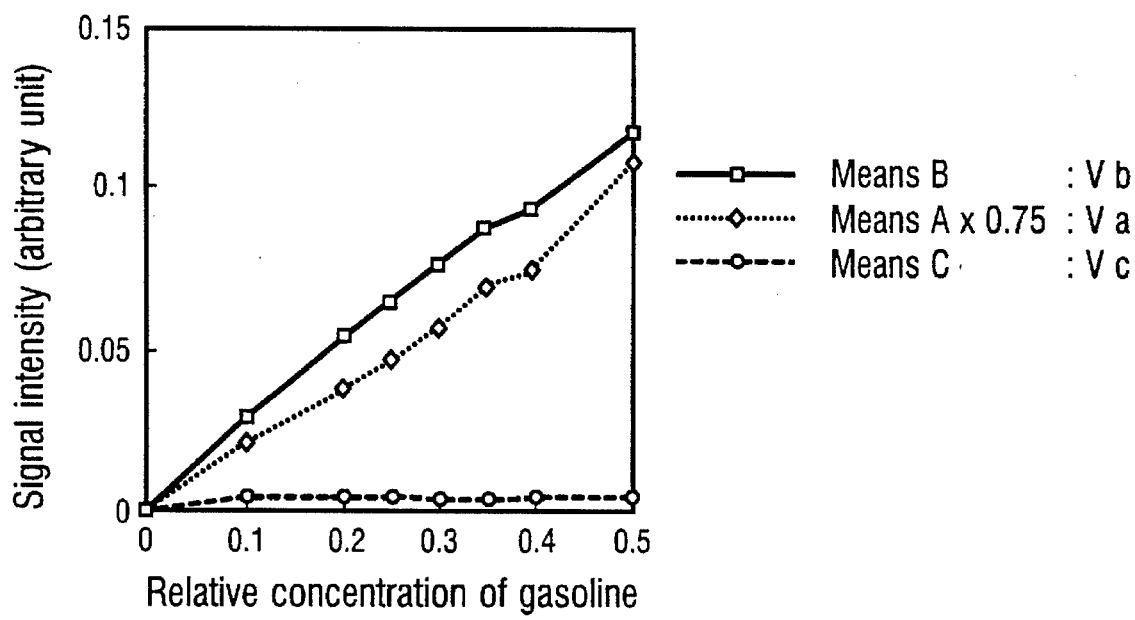
FIG. 12 shows the sensitivity-to-gasoline characteristics of the measuring means A, B and C used in Example 2.
Figure 13:
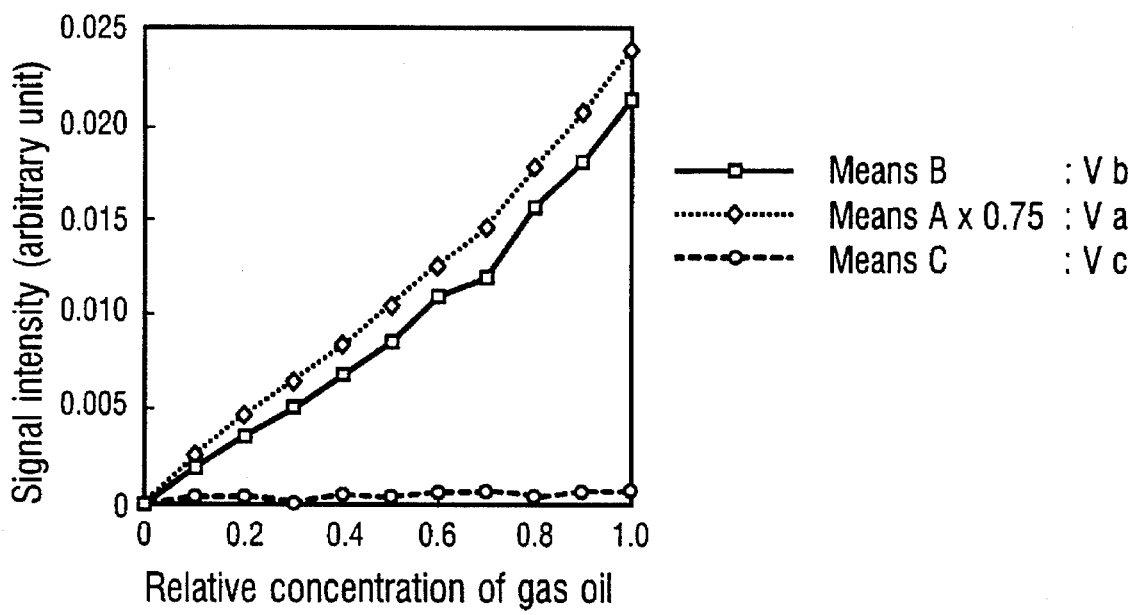
FIG. 13 shows the sensitivity-to-gas oil characteristics of the measuring means A, B and C used in Example 2.
Figure 14:
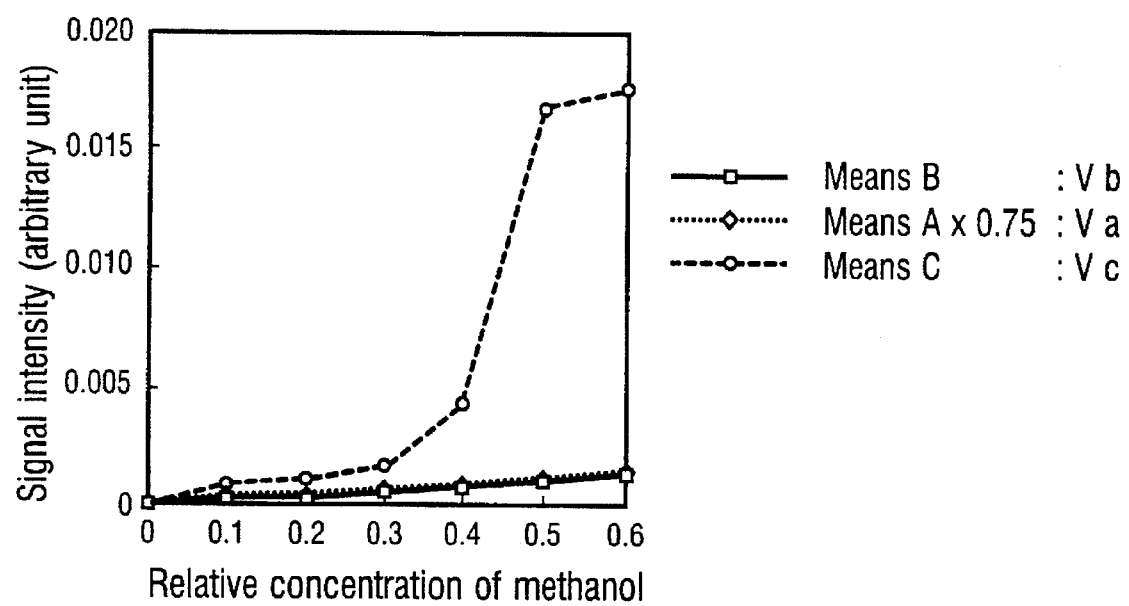
FIG. 14 shows the sensitivity-to-methanol characteristics of the measuring means A, B and C used in Example 2.

The sensitivity characteristics of the three measuring means to gasoline, diesel oil and methanol vapors were measured as in Example 1 and the results are shown in FIGS. 12–14, respectively. In each of these figures, the output values of measuring means A are plotted as multiplied by 0.75 (Va) whereas the output values of measuring means B and C are plotted as such (Vb and Vc). The terms "sensitivity" and "relative concentration" have the same meanings as defined in Example 1.

The results shown in FIGS. 12–14 indicate the following: if the relationship between the magnitudes of outputs from the respective measuring means as determined by the output comparator means is Vc>Va>Vb or Vc>Vb>Va, one may safely conclude that the vapor of interest is methanol vapor; if the output relationship is Va>Vb>Vc or Va>Vc>Vb, the vapor of interest may well be identified as gasoline vapor; if Vb>Va>Vc or Vb>Vc>Va, diesel oil vapor may be the identity of the vapor being measured.

EXAMPLE 3

Figure 15:
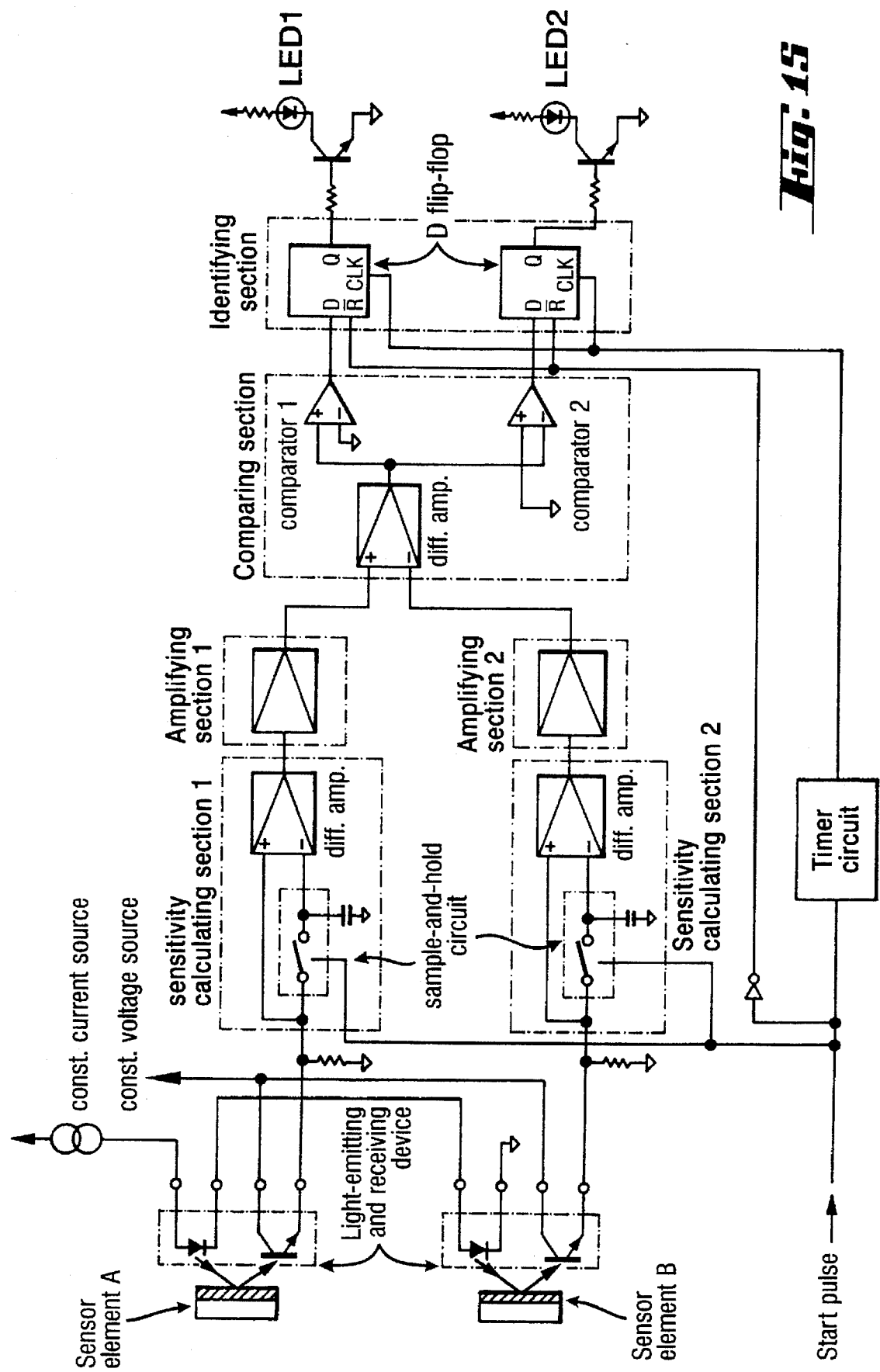
FIG. 15 shows the block diagram of the output comparator means used in Example 3.
Figure 16:
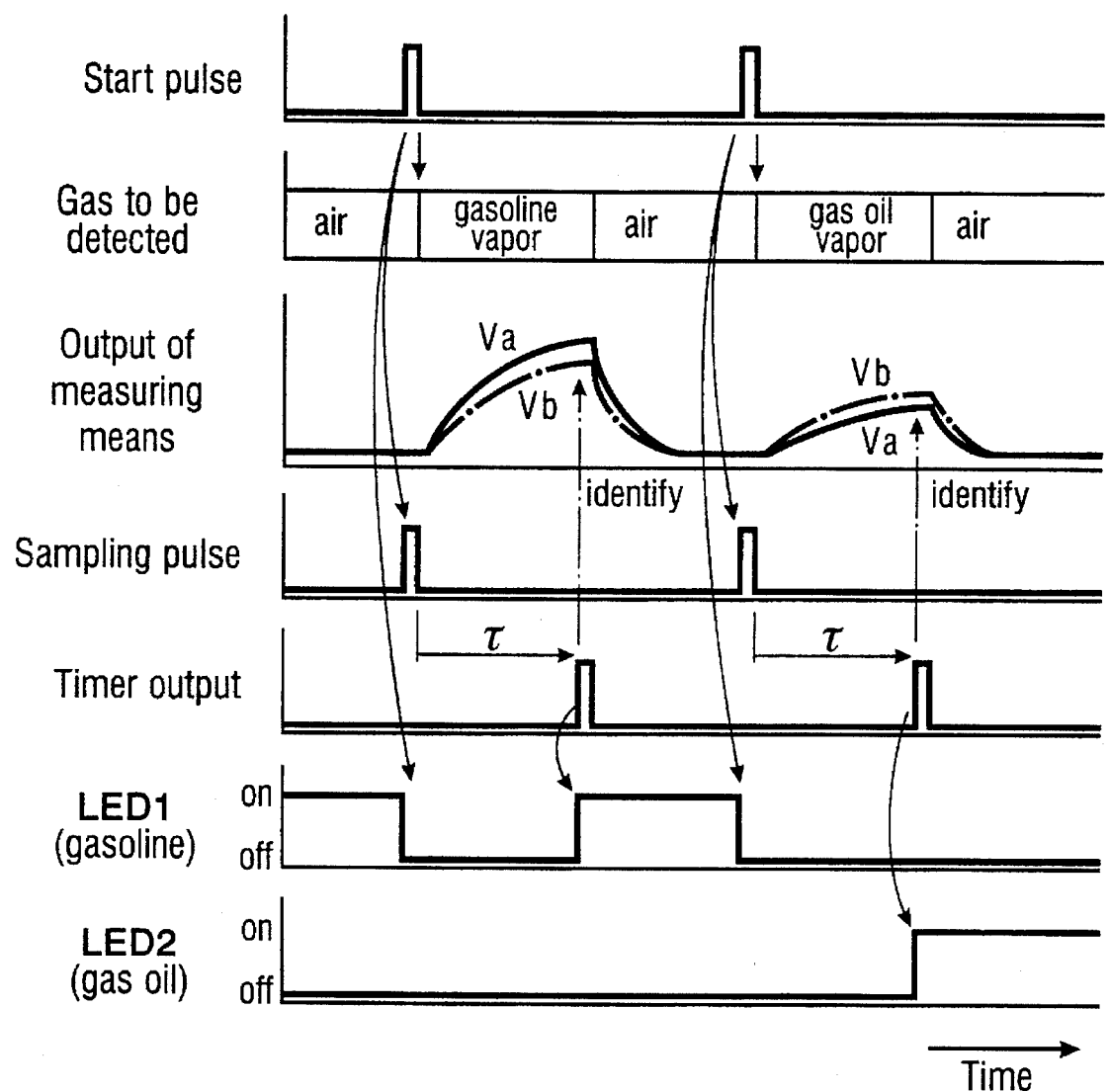
FIG. 16 shows the time sequence of the operation of the output comparator means.

FIG. 15 is a block diagram of the output comparator means used in distinguishing the vapor of a single fuel selected from the group consisting of two fuels. FIG. 16 is a timing chart showing the operational sequence of this output comparator means. As shown in FIG. 15, the comparator means is composed of two lines of sensitivity calculating section, two lines of amplifying section, a comparing section and an distinguishing section.

The operation of the output comparator means will now be described on a time basis with reference made to FIGS. 15 and 16.

The operation starts in response to an externally applied start pulse which performs the following three functions: i) resetting the result of identification by resetting the D flip-flops in the comparing section so as to turn off both LEDs 1 and 2; ii) sending a sampling signal to the sample-and-hold circuits in the sensitivity calculating section, thereby insuring that the outputs of the respective measuring means that have aspirated fuel vapor free air are stored in the associated hold capacitors so that the sensitivity calculating section is capable of outputting the difference from the output of each measuring means in response to air; and iii) instructing a gas switching mechanism (not shown) for aspiration of the gas of interest rather than air in synchronism with the pulse fall time. The switching mechanism will revert to the air aspiration mode after the lapse of a predetermined time.

Following the issuance of a start pulse, the two lines of sensitivity calculating section continue to produce the difference from the output of each measuring means in response to air. The respective outputs from the measuring means are fed to the two lines of amplifying section where they are subjected to multiplication by the factors necessary for the respective measuring means.

The outputs from the two lines of amplifying section are sent to the comparing section for determining the relationships between the magnitudes of the respective outputs. In the comparing section, the difference between the two outputs is calculated with a differential amplifier and the sign of the difference is then subjected to calculation with two comparators. Stated more specifically, the output of the differential amplifier is connected to both the positive input terminal of comparator 1 and the negative input terminal of comparator 2, whereas the negative input terminal of comparator 1 and the positive input terminal of comparator 2 are connected to the ground. Therefore, if the output from the differential amplifier is positive (i.e., the output of amplifying section 1 is greater than that of amplifying section 2), comparator 1 outputs a digital signal of "HI" level whereas comparator 2 outputs a signal of "LO" level and vice versa if the output from the differential amplifier is negative.

The two lines of sensitivity calculating section and amplifying section, as well as the comparing section operate continuously following the application of a start pulse; in contrast, both LEDs for outputting the results of identification will remain off until after the timer circuit issues a signal. The timer circuit generates a pulse immediately before the gas switching mechanism effects switching to air as the gas to be aspirated. The generated pulse triggers the D flip-flops in the distinguishing section so that they deliver the outputs of the two comparators in the comparing section. The flip-flops are triggered by the rising of the pulse from the time circuit, so their outputs will be held until a next start pulse is issued even if the pulse from the timer circuit falls. Hence, the two LEDs connected to the outputs of the flip-flops will turn off in accordance with the results of identification. Thus, LED 1 turns on if the gas to be detected is gasoline vapor whereas LED 2 turns on if gas oil vapor is to be detected.

The output from the distinguishing section is a digital signal which can be produced from a TTL or COMS; alternatively, the distinguishing section may be connected to a relay that produces the output of interest as a contact signal or an additional circuit may be provided to produce the output as an instrumentation signal on the order of 4–20 mA; if necessary, the distinguishing section may be connected to an LED or some other device that produces the output as an optical digital signal.

EXAMPLE 4

The method of the invention was applied to distinguish between gasoline and diesel oil by using SPR with a He-Ne laser employed as a light source.

Two sensor elements were provided; they were measuring means A including a thin poly(octadecyl methacrylate-co-glycidyl methacrylate) film and measuring means B including a thin poly(2-ethylhexyl-co-glycidyl methacrylate) film. Each film was formed by spin coating in a thickness of about 50 nm on a thin silver film formed in a thickness of 50 nm on a slide glass by vacuum evaporation.

Figure 17:
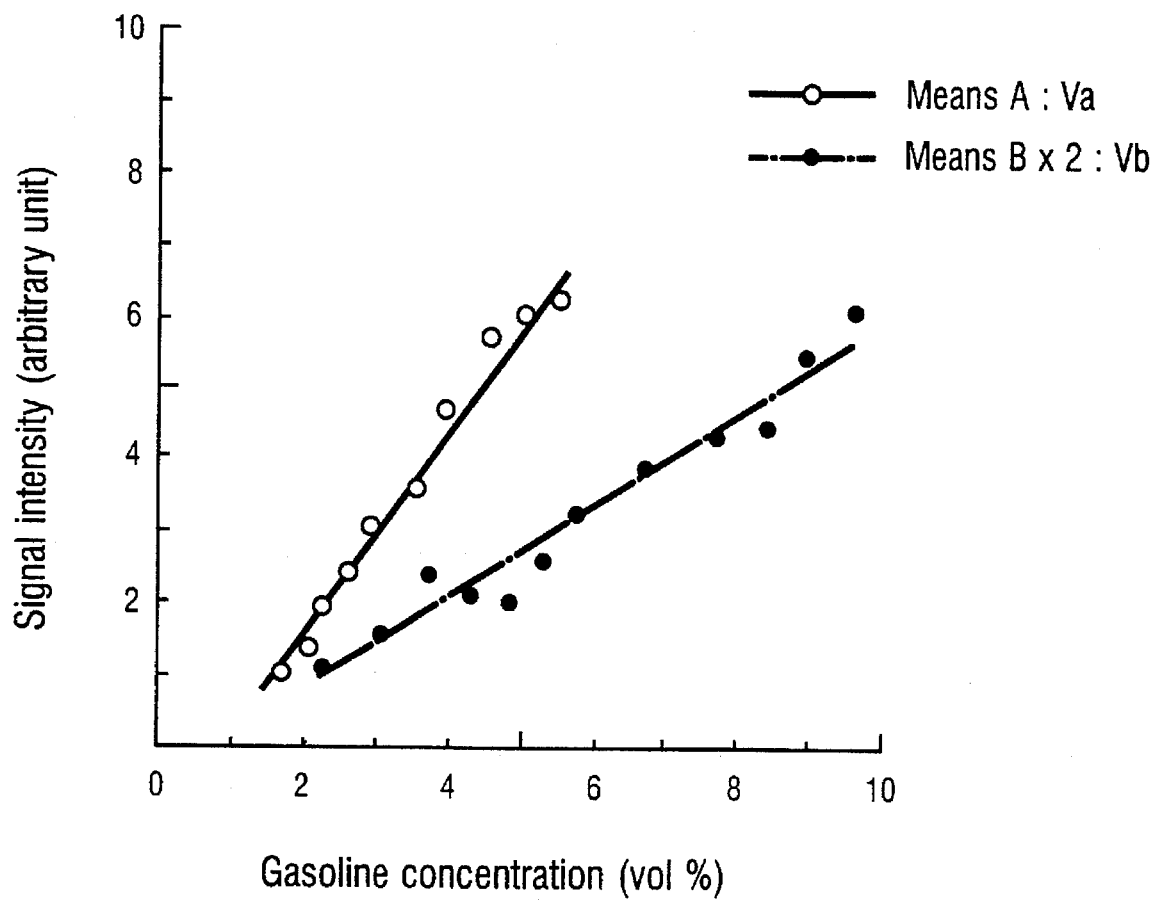
FIG. 17 shows the sensitivity-to-gasoline characteristics of the measuring means A and B used in Example 4.
Figure 18:
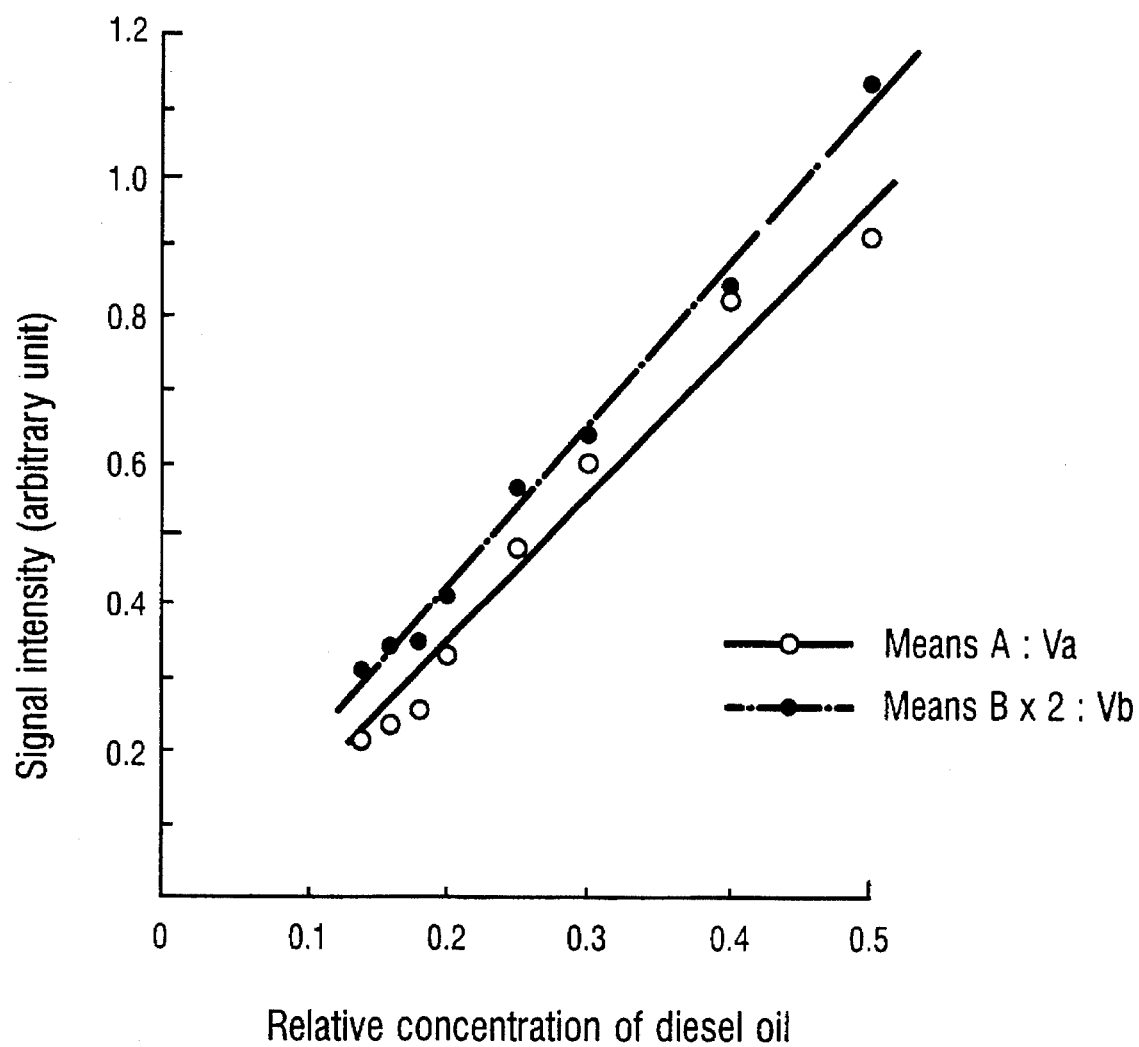
FIG. 18 shows the sensitivity-to-gas oil characteristics of the measuring means A and B used in Example 4.

The sensitivity characteristics of the two measuring means were measured to gasoline and gas oil vapors and the results are shown in FIGS. 17 and 18, respectively. In each of these figures, the output values of both measuring means A and B are plotted as multiplied by 2 (Va and Vb). The term "sensitivity" as used in connection with FIG. 17 means the concentration of gasoline vapor that was evolved by the same means as in Example 1 and which was measured with a commercial optical gas analyzer for gasoline (Model 18 of Riken Keiki Fine Instruments Co., Ltd.); the term "relative concentration" plotted along the horizontal axis of the graph in FIG. 18 has the same meaning as defined in Example 1.

The results shown in FIGS. 17 and 18 indicate the following: if the relationship between the magnitudes of outputs from the respective measuring means as determined by the output comparator means is Va>Vb, one may safely conclude that the vapor of interest is gasoline vapor; if Vb>Va, the vapor of interest may well be identified as gas oil vapor.

What is claimed is:

1. A method for distinguishing a single fuel vapor in an atmosphere of interest that is selected from the group consisting of at least two fuels and that is the sole fuel component of the atmosphere, comprising the steps of:

providing a plurality of measuring means that are at least equal in number to the types of fuels that compose the fuel group and which have different sensitivities to the respective fuel vapors;

presetting the relationship between the magnitudes of the outputs from the respective measuring means at various fuel vapor concentrations in such a manner that it differs from one fuel vapor to another;

placing said measuring means in the atmosphere of interest containing said single fuel vapor as the sole fuel component;

measuring the concentration of that fuel vapor;

determining the relationship between the magnitudes of outputs as obtained from the respective measuring means;

comparing the thus determined relationship with the preset relationships, thereby distinguishing the fuel vapor in the atmosphere of interest; and wherein each measuring means comprises a sensor element having a thin polymeric film on a substrate, and optical measuring means capable of optical measurement of physical changes comprising physical changes in thickness and refractive index that occur in the polymeric film.

2. A method according to claim 1 wherein the thin polymeric film is composed of a homo- or copolymer having a recurring unit represented by the following general formula (I):

wherein X is —H, —F, —Cl, —Br, —CH$_3$, —CF$_3$, —CN or —CH$_2$—CH$_3$; R$^1$ is —R$^2$ or —Z—R$^2$, wherein Z is —O—, —S—, —NH—, —NR$^{2'}$—, —(C=Y)—, —(C=Y)—Y—, —Y—(C=Y)—, —(SO$_2$)—, —Y'—(SO$_2$)—, —(SO$_2$)—Y'—, —Y'—(SO$_2$)—Y'—, —NH—(C=O)—, —(C=O)—NH—, —(C=O)—NR$^{2'}$—, —Y'—(C=Y)—Y'— or —O—(C=O)—(CH$_2$)$_n$—(C=O)—O— wherein Y is O or S, Y' is O or NH and n is an integer of 0 to 20, R$^2$ and R$^{2'}$ are each independently a hydrogen atom, linear alkyl group, branched alkyl group, cycloalkyl group, unsaturated hydrocarbon group, aryl group, saturated or unsaturated hetero ring group or substituted forms thereof;

provided that $R_1$ is not a hydrogen atom, a linear alkyl group or a branched alkyl group.

3. A method according to claim 2 wherein the physical changes in the thin polymeric film are those which occur as a result of said polymeric film having reacted with the fuel vapor of interest or those which are caused by its absorption by or adsorption on the film.

4. A method according to claim 2 wherein the physical changes in the thin polymeric film are those in the multiplicative product of the thickness and refractive index of said polymeric film.

5. A method according to claim 2 which uses interference enhanced reflection as the optical measuring means.

6. A method according to claim 2 which uses surface plasmon resonance as the optical measuring means.

7. A method according to claim 2 which uses optically guided Mach-Zehnder interferometry as the optical measuring means.

8. A method according to claim 1 wherein the determination of the relationship between the magnitudes of outputs as obtained from the respective measuring means is preceded by multiplication of each of said outputs by a proportionality constant.

9. A method according to claim 1 wherein the fuel to be identified is selected from the group consisting of gasoline, gas oil and methanol and wherein three units of the measuring means are employed.

10. A method according to claim 1 wherein the fuel to be identified is selected from the group consisting of gasoline and gas oil and wherein two units of the measuring means are employed.

11. A method according to claim 1 which further includes the step of outputting the result of fuel identification as either an electric or optical signal.

12. An apparatus for distinguishing a single fuel vapor in an atmosphere of interest that is selected from the group consisting of at least two fuels and that is the sole fuel component of the atmosphere, comprising:

a plurality of measuring means at least equal in number to the type of fuels that compose the fuel group, and output comparator means for comparing the magnitudes of the outputs from the respective measuring means;

said measuring means having different sensitivities to the concentrations of the respective fuel vapors;

said output comparing means being so adapted that the relationship between the magnitudes of the outputs from the respective measuring means at various fuel vapor concentrations is preset to differ from one fuel vapor to another, determining the relationship between the magnitudes of outputs as obtained from the respective measuring means, and comparing the thus determined relationship with the preset relationships, thereby distinguishing the type of the fuel vapor of interest; and wherein each measuring means comprises a sensor element having a thin polymeric film on a substrate, and optical measuring means capable of optical measurement of physical changes comprising physical changes in thickness and refractive index that occur in the polymeric film.

13. An apparatus according to claim 12 wherein the thin polymeric film is composed of a homo- or copolymer having a recurring unit represented by the following general formula (I):

wherein X is —H, —F, —Cl, —Br, —$CH_3$, —$CF_3$, —CN or —$CH_2$—$CH_3$; $R^1$ is —$R^2$ or —Z—$R^2$, wherein Z is —O—, —S—, —NH—, —$NR^{2'}$—, —(C=Y)—, —(C=Y)—Y—, —Y—(C=Y)—, —($SO_2$)—, —Y'—($SO_2$)—, —($SO_2$)—Y'—, —Y'—($SO_2$)—Y'—, —NH—(C=O)—, —(C=O)—NH—, —(C=O)—$NR^{2'}$—, —Y'—(C=Y)—Y'— or —O—(C=O)—($CH_2$)$_n$—(C=O)—O— wherein Y is O or S, Y' is O or NH and n is an integer of 0 to 20, $R^2$ and $R^{2'}$ are each independently a hydrogen atom, linear alkyl group, branched alkyl group, cycloalkyl group, unsaturated hydrocarbon group, aryl group, saturated or unsaturated hereto ring group or substituted forms thereof;

provided that $R_1$ is not a hydrogen atom, a linear alkyl group or a branched alkyl group.

14. An apparatus according to claim 12 wherein the physical changes in the thin polymeric film are those which occur as a result of said polymeric film having reacted with the fuel vapor of interest or those which are caused by its absorption by or adsorption on the film.

15. An apparatus according to claim 12 wherein the physical changes in the thin polymeric film are those in the multiplicative product of the thickness and refractive index of said polymeric film.

16. An apparatus according to claim 12 which uses interference enhanced reflection as the optical measuring means.

17. An apparatus according to claim 12 which uses surface plasmon resonance as the optical measuring means.

18. An apparatus according to claim 12 which uses optically guided Mach-Zehnder interferometry as the optical measuring means.

19. An apparatus according to claim 12 wherein the output comparator means performs determination of the relationship between the magnitudes of outputs from the respective measuring means only after multiplying each of said outputs by a proportionality constant.

20. An apparatus according to claim 12 wherein the fuel to be identified is selected from the group consisting of gasoline, gas oil and methanol and wherein three units of the measuring means are employed.

21. An apparatus according to claim 12 wherein the fuel to be identified is selected from the group consisting of gasoline and gas oil and wherein two units of the measuring means are employed.

22. An apparatus according to claim 12 which further includes means for outputting the result of fuel identification by the output comparator means as either an electric or optical signal.

23. A method for distinguishing a single fuel vapor in an atmosphere of interest that is selected from the group consisting of at least two fuels and that is the sole fuel component of the atmosphere, comprising the steps of:

providing a plurality of measuring means that are at least equal in number to the types of fuels that compose the fuel group and which have different sensitivities to the respective fuel vapors;

presetting the relationship between the magnitudes of the outputs from the respective measuring means at various fuel vapor concentrations in such a manner that if differs from one fuel vapor to another;

placing said measuring means in the atmosphere of interest containing said single fuel vapor as the sole fuel component;

measuring the concentration of the fuel vapor;

determining the relationship between the magnitudes of outputs as obtained from the respective measuring means; and comparing the thus determined relationship with the preset relationships, thereby distinguishing the fuel vapor in the atmosphere of interest; and wherein the thin polymeric film is composed of a homo- or copolymer having a recurring unit represented by the following general formula (I):

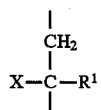  (I)

wherein X is —H, —F, —Cl, —Br, —CH$_3$, —CF$_3$, —CN or —CH$_2$—CH$_3$; R$^1$ is —R$^2$ or —Z—R$^2$, wherein Z is —O—, —S—, —NH—, —NR$^{2'}$—, —(C=Y)—, —(C=Y)—Y—, —Y—(C=Y)—, —(SO$_2$)—, —Y$^1$—(SO$_2$)—, —(SO$_2$)—Y'—, —Y'—(SO$_2$)—Y—', —NH—(C=O)—, —(C=O)—NH—, —(C=O)—NR$^{2'}$—, Y'—(C=Y)—Y'— or —O—(C=O)—(CH$_2$)$_n$—(C=O)—O— wherein Y or O or S, Y' is O or NH and n is an integer of 0 to 20, R$^2$ and R$^{2'}$ are each independently a hydrogen atom, linear alkyl group, branched alkyl group, cycloalkyl group, unsaturated hydrocarbon group, aryl group, saturated or unsaturated hetero ring group or substituted forms thereof;

provided that R$_1$ is not a hydrogen atom, a linear alkyl group or a branched alkyl group.

24. A method for distinguishing a single fuel vapor in an atmosphere of interest that is selected from the group consisting of at least two fuels and that is the sole fuel component of the atmosphere, comprising the steps of:

providing a plurality of measuring means that are at least equal in number to the types of fuels that compose the fuel group and which have different sensitivities to the respective fuel vapors;

presetting the relationship between the magnitudes of the outputs from the respective measuring means at various fuel vapor concentrations in such a manner that it differs from one fuel vapor to another;

placing said measuring means in the atmosphere of interest containing said single fuel vapor as the sole fuel component;

measuring the concentration of that fuel vapor;

determining the relationship between the magnitudes of outputs as obtained from the respective measuring means; and comparing the thus determined relationship with the preset relationships, thereby distinguishing the fuel vapor in the atmosphere of interest;

wherein each measuring means comprises a sensor element having a thin polymeric film on a substrate, and optical measuring means capable of optical measurement of physical changes that occur in the polymeric film; and wherein the physical changes in the thin polymeric film are those in the multiplicative product of the thickness and refractive index of said polymeric film.

25. A method for distinguishing a single fuel vapor in an atmosphere of interest that is selected from the group consisting of at least two fuels and that is the sole fuel component of the atmosphere, comprising the steps of:

providing a plurality of measuring means that are at least equal in number to the types of fuels that compose the fuel group and which have different sensitivities to the respective fuel vapors;

presetting the relationship between the magnitudes of the outputs from the respective measuring means at various fuel vapor concentrations in such a manner that it differs from one fuel vapor to another;

placing said measuring means in the atmosphere of interest containing said single fuel vapor as the sole fuel component;

measuring the concentration of that fuel vapor;

determining the relationship between the magnitudes of outputs as obtained from the respective measuring means; and comparing the thus determined relationship with the preset relationships, thereby distinguishing the fuel vapor in the atmosphere of interest; and wherein each measuring means comprises a sensor element having a thin polymeric film on a substrate, and optical measuring means capable of optical measurement of physical changes that occur in the polymeric film and wherein interference enhanced reflection is used as the optical measuring means.

26. A method for distinguishing a single fuel vapor in an atmosphere of interest that is selected from the group consisting of at least two fuels and that is the sole fuel component of the atmosphere, comprising the steps of:

providing a plurality of measuring means that are at least equal in number to the types of fuels that compose the fuel group and which have different sensitivities to the respective fuel vapors;

presetting the relationship between the magnitudes of the outputs from the respective measuring means at various fuel vapor concentrations in such a manner that it differs from one fuel vapor to another;

placing said measuring means in the atmosphere of interest containing said single fuel vapor as the sole fuel component;

measuring the concentration of that fuel vapor;

determining the relationship between the magnitudes of outputs as obtained from the respective measuring means;

comparing the thus determined relationship with the preset relationships, thereby distinguishing the fuel vapor in the atmosphere of interest; and wherein each measuring means comprises a sensor element having a thin polymeric film on a substrate, and optical measuring means capable of optical measurement of physical changes that occur in the polymeric film and wherein surface plasmon resonance is used as the optical measuring means.

27. A method for distinguishing a single fuel vapor in an atmosphere of interest that is selected from the group consisting of at least two fuels and that is the sole fuel component of the atmosphere, comprising the steps of:

providing a plurality of measuring means that are at least equal in number to the types of fuels that compose the fuel group and which have different sensitivities to the respective fuel vapors;

presetting the relationship between the magnitudes of the outputs from the respective measuring means at various fuel vapor concentrations in such a manner that it differs from one fuel vapor to another;

placing said measuring means in the atmosphere of interest containing said single fuel vapor as the sole fuel component;

measuring the concentration of that fuel vapor;

determining the relationship between the magnitudes of outputs as obtained from the respective measuring means;

comparing the thus determined relationship with the preset relationships, thereby distinguishing the fuel vapor in the atmosphere of interest; and wherein each measuring means comprises a sensor element having a thin polymeric film on substrate, and optical measuring means capable of optical measurement of physical changes that occur in the polymeric film, and wherein optically guided Mach-Zehnder interferometry is used as the optical measuring means.

28. An apparatus for distinguishing a single fuel vapor in an atmosphere of interest that is selected from the group consisting of at least two fuels and that is the sole fuel component of the atmosphere, comprising:

a plurality of measuring means at least equal in number to the types of fuels that compose the fuel group, and output comparator means for comparing the magnitudes of the outputs from the respective measuring means;

said measuring means having different sensitivities to the concentrations of the respective fuel vapors;

said output comparing means being so adapted that the relationship between the magnitudes of the outputs from the respective measuring means at various fuel vapor concentrations is preset to differ from one fuel vapor to another, determining the relationship between the magnitudes of outputs as obtained from the respective measuring means, and comparing the thus determined relationship with the preset relationships, thereby distinguishing the type of the fuel vapor of interest; and wherein the thin polymeric film is composed of a homo- or copolymer having a recurring unit represented by the following general formula (I):

wherein X is —H, —F, —Cl, —Br, —CH$_3$, —CF$_3$, —CN or —CH$_2$—CH$_3$; R$^1$ is —R$^2$ or —Z—R$^2$, wherein Z is —O—, —S—, —NH—, NR$^{2'}$—, —(C=Y)—, —(C=Y)—Y—, —Y—(C=Y)—, —(SO$_2$)—, —Y$^1$—(SO$_2$), —(SO$_2$)—Y'—, —Y'—(SO$_2$)—Y'—, —NH—(C=O)—, —(C=O)—NH—, —(C=O)—NR$^{2'}$—, —Y'—(C=Y)—Y'— or —O—(C=O)—(CH$_2$)$_n$—(C=O)—O— wherein Y is O or S, Y' is O or NH and n is an integer of 0 to 20, R$^2$ and R$^{2'}$ are each independently a hydrogen atom, linear alkyl group, branched alkyl group, cycloalkyl group, unsaturated hydrocarbon group, aryl group, saturated or unsaturated hetero ring group or substituted forms thereof;

provided that R$_1$ is not a hydrogen atom, a linear alkyl group or a branched alkyl group.

29. An apparatus for distinguishing a single fuel vapor in an atmosphere of interest that is selected from the group consisting of at least two fuels and that is the sole fuel component of the atmosphere, comprising:

a plurality of measuring means at least equal in number to the types of fuels that compose the fuel group, and output comparator means for comparing the magnitudes of the outputs from the respective measuring means;

said measuring means having different sensitivities to the concentrations of the respective fuel vapors;

said output comparing means being so adapted that the relationship between the magnitudes of the outputs from the respective measuring means at various fuel vapor concentrations is preset to differ from one fuel vapor to another, determining the relationship between the magnitudes of outputs as obtained from the respective measuring means, and comparing the thus determined relationship with the preset relationships, thereby distinguishing the type of the fuel vapor of interest; and wherein each measuring means comprises a sensor element having a thin polymeric film on a substrate, and optical measuring means capable of optical measurement of physical changes that occur in the polymeric film; and wherein the physical changes in the thin polymeric film are those in the multiplicative product of the thickness and refractive index of said polymeric film.

30. An apparatus for distinguishing a single fuel vapor in an atmosphere of interest that is selected from the group consisting of at least two fuels and that is the sole fuel component of the atmosphere, comprising:

a plurality of measuring means at least equal in number to the types of fuels that compose the fuel group, and output comparator means for comparing the magnitudes of the outputs from the respective measuring means;

said measuring means having different sensitivities to the concentrations of the respective fuel vapors;

said output comparing means being so adapted that the relationship between the magnitudes of the outputs from the respective measuring means at various fuel vapor concentrations is preset to differ from one fuel vapor to another, determining the relationship between the magnitudes of outputs as obtained from the respective measuring means, and comparing the thus determined relationship with the preset relationships, thereby distinguishing the type of the fuel vapor of interest; and wherein each measuring means comprises a sensor element having a thin polymeric film on a substrate, and optical measuring means capable of optical measurement of physical changes that occur in the polymeric film and wherein interference enhanced reflection is used as the optical measuring means.

31. An apparatus for distinguishing a single fuel vapor in an atmosphere of interest that is selected from the group consisting of at least two fuels and that is the sole fuel component of the atmosphere, comprising:

a plurality of measuring means at least equal in number to the types of fuels that compose the fuel group, and output comparator means for comparing the magnitudes of the outputs from the respective measuring means;

said measuring means having different sensitivities to the concentrations of the respective fuel vapors;

said output comparing means being so adapted that the relationship between the magnitudes of the outputs from the respective measuring means at various fuel vapor concentrations is preset to differ from one fuel vapor to another, determining the relationship between the magnitudes of outputs as obtained from the respective measuring means, and comparing the thus determined relationship with the preset relationships, thereby distinguishing the type of the fuel vapor of interest; and wherein each measuring means comprises a sensor element having a thin polymeric film on a substrate, and optical measuring means capable of optical measurement of physical changes that occur in the polymeric film, and wherein surface plasmon resonance is used as the optical measuring means.

32. An apparatus for distinguishing a single fuel vapor in an atmosphere of interest that is selected from the group consisting of at least two fuels and that is the sole fuel component of the atmosphere, comprising:

a plurality of measuring means at least equal in number to the types of fuels that compose the fuel group, and output comparator means for comparing the magnitudes of the outputs from the respective measuring means;

said measuring means having different sensitivities to the concentrations of the respective fuel vapors;

said output comparing means being so adapted that the relationship between the magnitudes of the outputs from the respective measuring means at various fuel vapor concentrations is preset to differ from one fuel vapor to another, determining the relationship between the magnitudes of outputs as obtained from the respective measuring means, and comparing the thus determined relationship with the preset relationships, thereby distinguishing the type of the fuel vapor of interest; and wherein each measuring means comprises a sensor element having a thin polymeric film on a substrate, and optical measuring means capable of optical measurement of physical changes that occur in the polymeric film, and wherein optically guided Mach-Zehnder interferometry is used as the optical measuring means.

* * * * *